United States Patent [19]

Reinhardt et al.

[11] Patent Number: 5,833,657
[45] Date of Patent: Nov. 10, 1998

[54] SINGLE-WALLED BALLOON CATHETER WITH NON-LINEAR COMPLIANCE CHARACTERISTIC

[75] Inventors: Robert W. Reinhardt, Chatham; Nicholas A. Green, Kinnelon, both of N.J.

[73] Assignee: Ethicon, Inc., Somerville, N.J.

[21] Appl. No.: 642,365

[22] Filed: May 3, 1996

Related U.S. Application Data

[63] Continuation-in-part of Ser. No. 453,837, May 30, 1995, abandoned.

[51] Int. Cl.⁶ ................................................. A61M 29/00
[52] U.S. Cl. ............................ 604/96; 606/192; 606/198
[58] Field of Search .................... 605/96, 101; 606/192, 606/198

[56] References Cited

U.S. PATENT DOCUMENTS

| | | | |
|---|---|---|---|
| 5,254,090 | 10/1993 | Lombardi et al. | 604/96 |
| 5,270,086 | 12/1993 | Hamlin | 604/96 |
| 5,348,538 | 9/1994 | Wang et al. | 604/96 |
| 5,478,349 | 12/1995 | Nicholas | 606/198 |
| 5,490,839 | 2/1996 | Wang et al. | 604/96 |
| 5,554,120 | 9/1996 | Chen et al. | 604/96 |
| 5,587,125 | 12/1996 | Roychowdhury | 604/96 |

*Primary Examiner*—Michael Powell Buiz
*Assistant Examiner*—Julian W. Woo
*Attorney, Agent, or Firm*—Paul A. Coletti

[57] ABSTRACT

A balloon element for use in a catheter has a multi-layered single-walled structure and a compliance characteristic exhibiting a first, non-compliant region at low operating pressures and a secondary compliant region at higher operating pressures. The properties of the balloon element permit it to serve for both dilatation of bodily vessels and stent delivery and implantation. A method of manufacturing the balloon element involves extrusion of a tube of material, such as PEEK, which serves as an inner wall layer of the finished balloon element and provides the desired strength and compliance characteristics of the balloon element, and a post-extrusion over the first tube, which provides an outer wall layer in the finished balloon element imparting abrasion resistance and other desirable mechanical properties.

9 Claims, 5 Drawing Sheets

SINGLE-WALLED BALLOON CATHETER WITH NON-LINEAR COMPLIANCE CHARACTERISTIC

RELATED APPLICATION

This is a continuation in-part of application Ser. No. 08/453,837, filed May 30, 1995, now abandoned.

FIELD OF THE INVENTION

This invention relates in general to balloon catheters and to catheter assemblies having an inflatable balloon element. More particularly, this invention relates to multi-layered single-walled balloon catheter elements having unique properties which enable them to serve for both dilatation and stent delivery and implantation.

BACKGROUND OF THE INVENTION

The use of balloon catheters for high pressure dilatation of occluded bodily vessels, such as arteries and the like, is well known. Balloon coronary angioplasty, for example, is used as an alternative to open-heart coronary bypass surgery. This technique typically involves routing a dilatation catheter, with an inflatable expander member (balloon) on its distal end, through the vascular system to a location within a coronary artery containing a stenotic lesion. The balloon is then positioned so as to span the lesion. An inflation fluid, usually a liquid, is then introduced into the proximal end of the catheter to inflate the balloon to a predetermined elevated pressure whereby the lesion is compressed into the vessel wall, restoring patency to the previously occluded vessel. The balloon is then deflated and the catheter is removed. The inflation fluid is usually applied at relatively high pressures, typically in the range of from about six to about twelve atmospheres.

Balloon angioplasty sometimes results in short or long term failure. That is, vessels may abruptly close shortly after the procedure or gradual restenosis may occur up to several months afterward.

To counter the tendency of recurrent vessel occlusion following balloon angioplasty, implantable endoluminal prostheses, commonly referred to as grafts or stents, have emerged as a means by which to achieve long term vessel patency. Stated simply, a stent functions as permanent scaffolding to structurally support the vessel wall and thereby maintain coronary luminal patency.

Although the present invention is not directed to stent delivery systems, as such, it would perhaps be helpful to an understanding of the invention to briefly describe here the operation of such a system.

In a typical stent implantation procedure, implantation immediately follows a balloon angioplasty. Angioplastic dilatation of the lesion produces a residual lumen large enough to accept a stent-carrying balloon dilatation catheter and a delivery sheath which surrounds the catheter and passes through an exterior guide catheter. The apparatus and methods used to place an arterial stent are therefore in many respects similar to those used in the angioplasty procedure itself.

Typically, following angioplasty, an exterior guide catheter remains in position when the angioplasty catheter and its deflated balloon are withdrawn and discarded. A stent delivery system may then be routed through the guide catheter to a position in which its distal end is disposed substantially coextensively with the distal end of the guide catheter and immediately proximate, i.e., upstream of, the previously expanded lesion.

Once properly positioned relative to the guide catheter, the stent delivery system is extended from the distal end of the guide catheter until the stent spans the previously expanded lesion. A delivery sheath, which is slideable relative to the delivery catheter, balloon and stent, is then withdrawn into the guide catheter to expose the balloon and stent. The delivery catheter is then supplied with a pressurized fluid, which expands the balloon and the associated stent to a desired diameter sufficient to exceed the elastic limit of the stent. The stent thus becomes embedded in and permanently supports the vessel wall. Typically, the balloon is then deflated and it, the delivery catheter and guide catheter are withdrawn, leaving the expanded stent and an open lumen.

Generally, a given balloon catheter has been able to accomplish only one of two functions. Either the balloon catheter is suitable for dilatation, as in angioplasty, valvuloplasty or urological uses, or it is suitable for use in a stent delivery system. Heretofore, the materials and constructions by which these expandable balloon catheters have been made have not provided a reliable dual function catheter. Typically, known catheters are not able to perform both functions acceptably or optimally. An advantage therefore exists for a balloon catheter capable of use at both low and high inflation pressures and with angioplasty and stent delivery, and at higher pressures and low compliance to further expand and implant the stent in post-delivery steps.

Balloons of the kind used in catheters are often described by means of their expansion characteristics, expressed numerically as a decimal portion of a millimeter that the balloon will expand from its initial (so-called "low pressure") diameter upon application of one additional atmosphere. A plot of the diameter of the balloon against the inflation pressure is called the compliance curve or expansion characteristic for that balloon. A balloon which produces a relatively large increase in diameter for a given increment in pressure is said to be highly compliant, to have a "high compliance curve", or in general to be a compliant balloon. If, on the other hand, a balloon exhibits a relatively small increase in diameter or a given increment in pressure, it is said to have a low compliance curve, or to be "non-compliant". In general, non-compliant balloons can be expected to increase in diameter by a maximum of five percent (5%) of their nominal initial diameter in response to increasing pressure throughout their operating range. High-complaint balloons, on the other hand, typically increase fifteen to forty percent (15–40%) throughout their operating range.

Those skilled in the art will appreciate that a non-compliant balloon, when inflated to its expanded diameter, is very hard and rigid, and capable of applying high local force to break hard lesions (such as calcified atheromas) without undue risk of damaging adjacent anatomical structures.

It is therefore a general object of the invention to provide a new and more useful balloon catheter and methods of making and using it. More specifically, it is an object of the invention to provide a balloon catheter, the characteristics of which allow a physician to perform an initial procedure involving dilatation, such as angioplasty, and to then accomplish a further two-stage procedure, such as placement of a device such as a stent within a lumen of the body followed by high pressure post-delivery dilatation to permanently implant the stent within the lumen at a desired diameter. The angioplasty may itself be a two-stage procedure, involving initial breaking of a hard lesion in the non-compliant range, followed by expansion of the lumen in the compliant range.

It is a further object of the invention to provide a balloon catheter made from a material which will not only feel "soft" within the body, but is also suitably resistant to bursting and puncturing.

It is another object of the invention to provide a unique method and combination of materials for forming a balloon catheter.

It is yet another object of the invention to provide a balloon catheter, the material and structure of which allows the physician to place the stent on the catheter and use the stent and catheter combination together to perform both a stent placement post-placement dilatation.

SUMMARY OF THE INVENTION

Another aspect of the invention is a novel method for forming a multi-layered expanded balloon for use with a medical catheter. This method comprises the steps of first forming a balloon from a first material having a high tensile strength and a low initial distensibility; next, folding the balloon to a configuration which I would be expected to assume initially in use; and finally coating the balloon in the folded state with a more readily distensible elastomeric second material. In a presently preferred form of the invention, the first material is PEEK, and the second material chosen from thermoplastics having melting points over than that of the first material. Multiple coatings for balloons are also feasible.

The above and other objects of the invention are accomplished by means of a multi-layered balloon catheter element, the inner layer of which is of a material exhibiting high tensile strength and, on initial inflation, low distensibility. The material of the tensile layer, for which polyether ether ketone (PEEK) has been found preferable and particularly well suited, provides, after a transition point, increased distensibility. Stated in other terms, the balloon element exhibits a compliance curve characterized by an initial region of low compliance (at relatively low inflation pressures), followed by a region of higher compliance at higher inflation pressures. Thus, the invention provides a balloon which can be expanded non-compliantly using relatively low pressures for procedures such as the initial stages of angioplasty or initial stent placement. Thereafter, the balloon can be inflated at much higher pressures to, as the case may be, further expand the lumen, or implant a stent.

As is described in greater detail below, the balloon element in accordance with the invention is also provided with a soft, more easily distensible, outer layer, which imparts to the finished balloon element a desirable puncture and abrasion resistance as well as a softness of "feel" within the body. The outer layer preferably has little, if any, effect on the expansion characteristics of the balloon but may be so applied as to provide the balloon with a "shape memory", which helps the balloon return to its original folded cross-sectional geometry when the balloon is deflated during or after use.

Balloon catheters intended for angioplasty, and having non-linear expansion characteristics, have heretofore been proposed, but none is believed capable of providing the versatility and relative simplicity of the present invention. For example, U.S. Pat. No. 5,348,538, issued Sep. 20, 1994, to Wang et al., and No. 5,447,497, issued Sep. 5, 1995, to Sogard et al., both disclose balloon catheters which are said to be compliant when first expanded (at relatively low inflation pressures), after which they became non-compliant. The latter patent also discloses, as an alternative embodiment, a balloon catheter having one balloon within the other, and said to be capable of providing a discontinuous non-linear compliance characteristic, such that the dual balloon at first has a non-compliant characteristic, and then, when subjected to internal pressure sufficient to actually burst one of the two balloons, to exhibit a compliant characteristic provided by the surviving balloon. With such an arrangement, so it is suggested, the inner balloon can be made of such a nominal diameter that initial inflation is compliant until actual rupture of the inner balloon, whereupon the pressure in the balloon is suddenly reduced. Further inflation of the intact outer balloon is said to follow a non-compliant characteristic.

The balloon element of the present invention can greatly simplify the surgical procedures in which it is used. More particularly, it will be seen that when using a balloon in accordance with the invention, there is no need to replace the balloon element with another element of different diameter if the first inflation of the element does not restore the desired patency of the lumen. Neither is it necessary to replace the balloon element to implant the stent after delivery. Other unexpected advantages flow from the novel construction of the present balloon. Use of a balloon element characterized by high tensile strength and low compliance at relatively low inflation pressures provides for precise and predictable adjustment of its expansion diameter during stent placement, while use of the same balloon element in the high compliance pressure range enables the physician to easily expand a placed stent to its final diameter.

DETAILED DESCRIPTION

Figure 1:
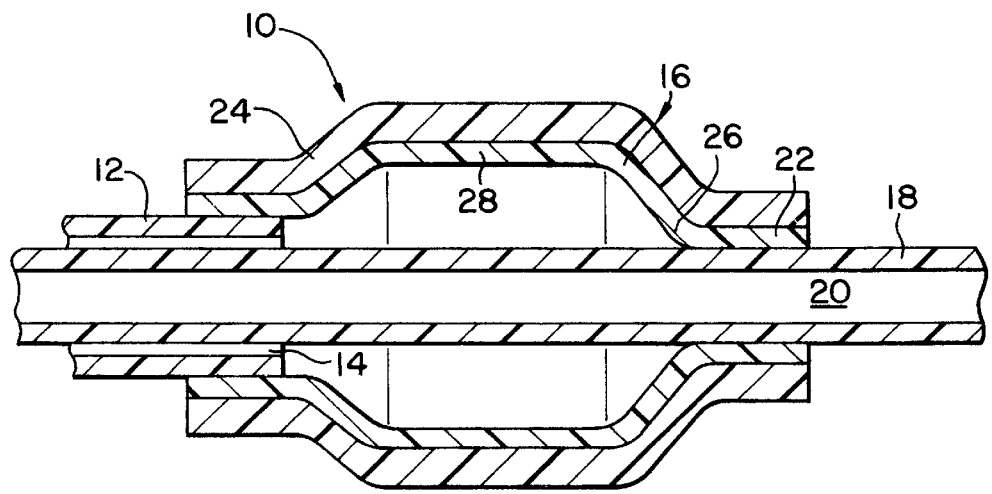
FIG. 1 is a longitudinal cross-sectional view, showing a portion of a balloon catheter, with an expander balloon element in accordance with the present invention.
Figure 2:
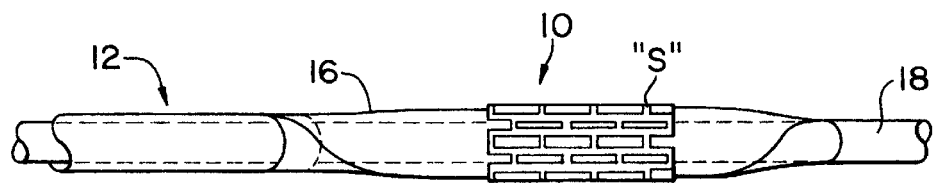
FIG. 2 is a side elevation view of a deflated balloon element of the present invention with a stent attached.
Figure 3:
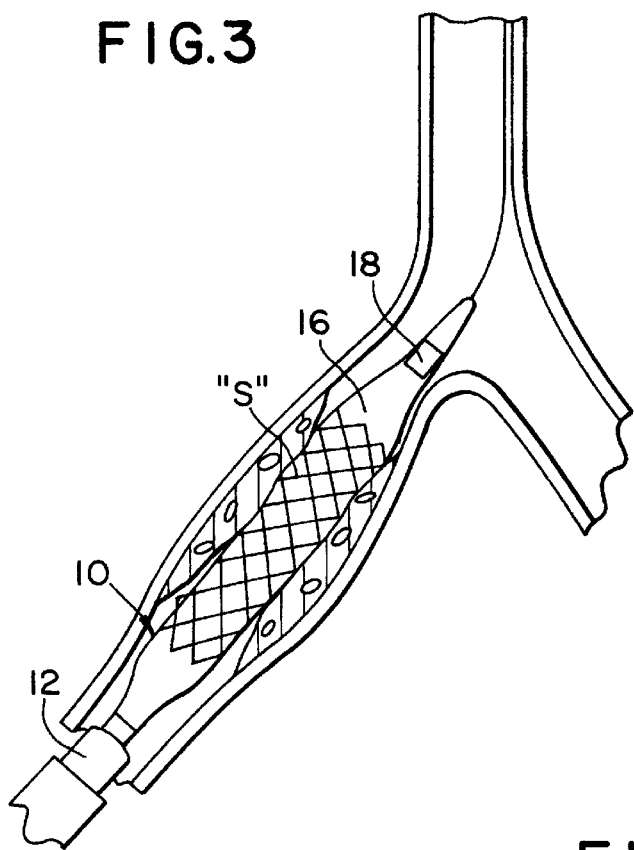
FIG. 3 is a side elevation view of the balloon of the present invention expanded to deliver and place a stent within a lumen of the body.

Referring now to the drawings in detail, wherein like reference numerals indicate like elements, there is seen in FIG. 1 a portion of a balloon catheter, designated generally by the reference numeral 10. It will be understood that balloon catheters may be used in angioplasty or in procedures involving other vascular systems or cavities of the body, and may be delivered over a guide wire for using other techniques familiar to those skilled in the art.

The balloon catheter 10 comprises an elongated tubular body 12, the distal end of which is seen in FIG. 1. Within the tubular body 12 is a lumen 14, which extends for the length of the tubular body 12.

Affixed to the distal end of the tubular body 12 is a balloon element 16. As is apparent from FIG. 1, the interior of the balloon element 16 is in fluid communication with the lumen 14, so that the lumen 14 can serve as a source of inflation fluid for the balloon element 16.

Also passing through the lumen 14 and concentric with the elongated tubular body 12 is an inner tubular body 18. The inner tubular body 18 itself provides a lumen 20.

A distal end 22 of the balloon element 16 is affixed, by adhesive (not shown) or other suitable bonding, to the outer surface of the inner tubular body 18.

The tubular body 12 and inner tubular body 18 are typically made of flexible and relatively strong structural materials such as high density polyethylene, although other suitable materials may be used.

As is apparent from FIG. 1, the balloon element 16 is generally cylindrical, with tapered neck portions 24 and 26 at its respective ends having diameters corresponding, respectively, to the outer diameters of the tubular body 14 and inner tubular body 18.

As will be described below, the balloon element 16 is molded to a desired shape and wall thickness. Those skilled in the art will appreciate that the expansion characteristic of the balloon is a function of, among other factors, the wall thickness and the material from which the balloon element is made.

The uninflated diameter of a typical balloon element 16 is substantially greater than the diameter of the tubular body 12 and inner tubular body 18 with which it is associated. Thus, it is conventional practice to fold the balloon element to form a series of lobes (typically from two to five) and to wrap the folded balloon element 16 around the tubular bodies (as in FIG. 7) to maintain a low uninflated profile. Low profile is a desirable characteristic of balloon elements.

The walls of the balloon element 16 are made up of at least an inner layer 28 and an outer layer 30, to be described in greater detail below. Additional wall layers may be used within the purview of the present invention.

Figure 4:
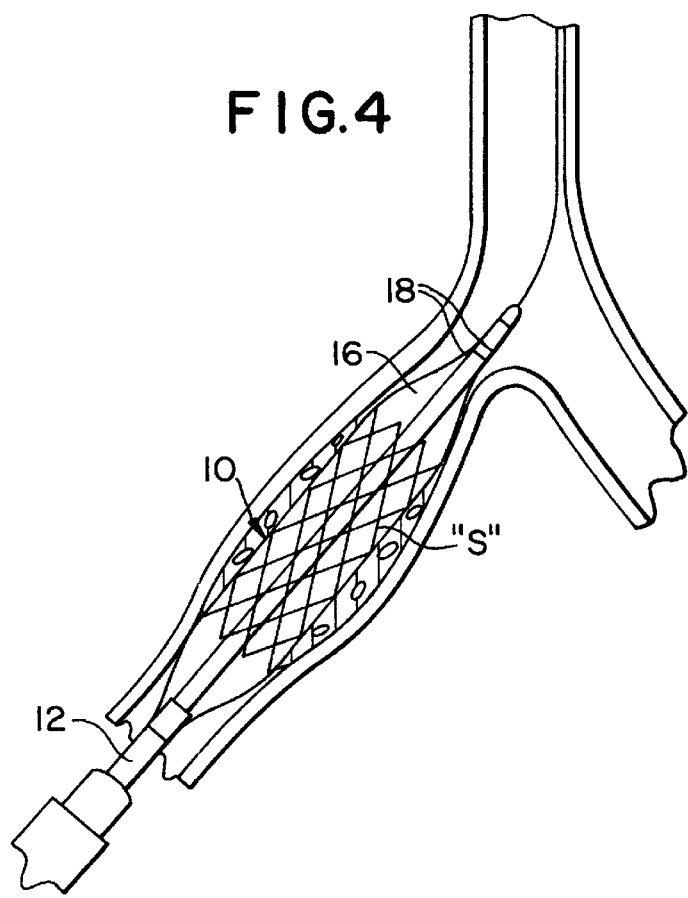
FIG. 4 is a side elevation view of the present invention expanded to further dilate and size the stent in the lumen.
Figure 5:
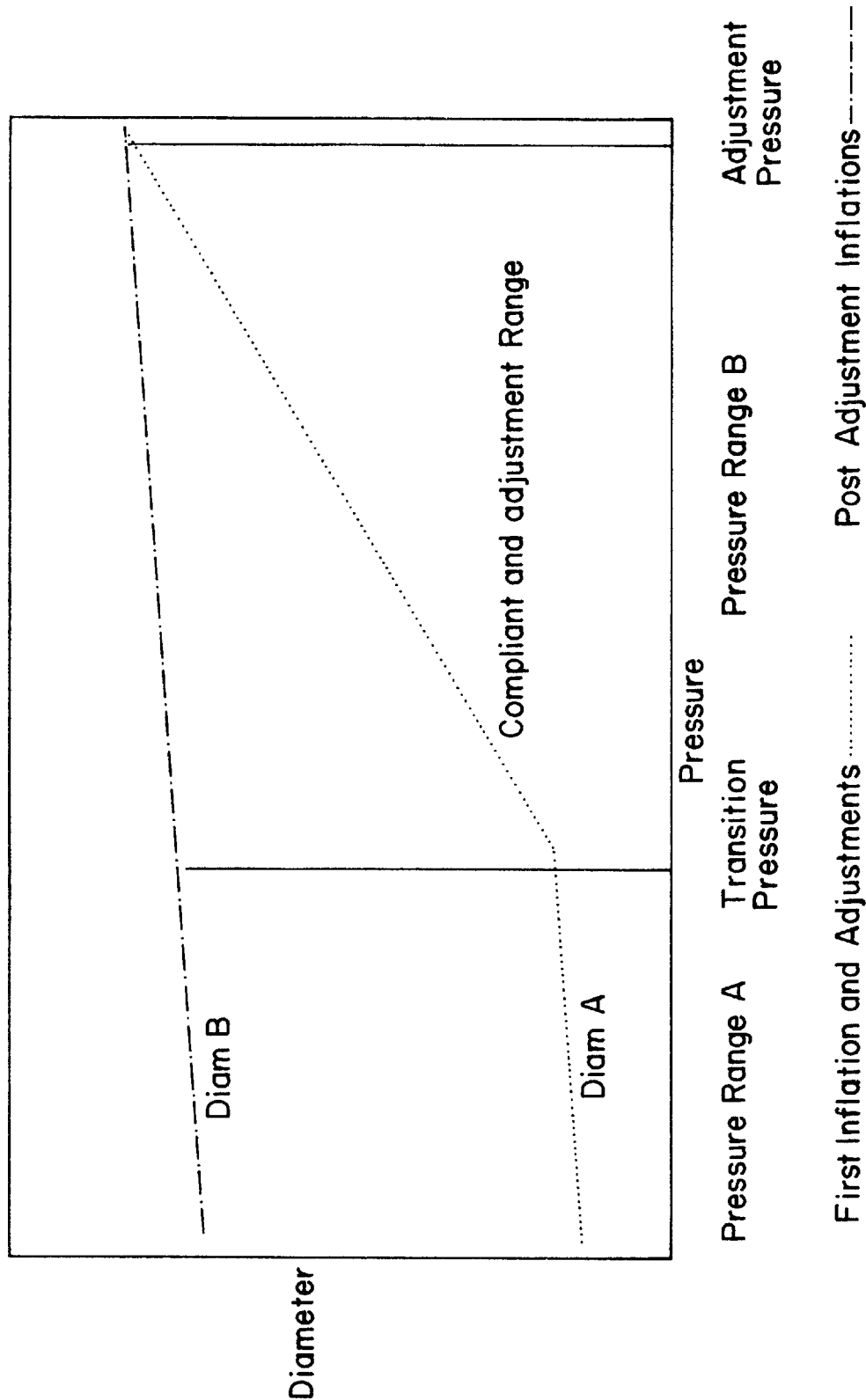
FIG. 5 is graph depicting, in idealized form, the expansion characteristics of a balloon element in accordance with the invention.

Referring now to FIG. 5, there is seen, graphically, an idealized depiction of the expansion characteristic of a balloon element 16 in accordance with the present invention. Thus, during the initial portion of the expansion of the balloon element 16 (labeled pressure range "A" in FIG. 4), the balloon expands non-compliantly in accordance with the pressure/diameter curve labeled "Diam. A". As will be seen, the balloon element takes on an expanded diameter which changes relatively little with the addition of inflation pressure. Adequate dilatation pressures and predictable diameters across a relatively wide range of pressure can be provided by the balloon element 16 within the pressure range "A", and it is within this pressure range that stent delivery can take place. If the surgeon wishes to further expand the stent, the surgeon applies pressure to the balloon element 16 beyond pressure range "A" and beyond a transition pressure "T" to a pressure range (labeled pressure range "B" in FIG. 4) in which the balloon element 16 exhibits a compliant characteristic.

Within pressure range B, the balloon may be caused to expand substantially beyond Diameter A, to adjust the balloon and stent diameter. In other words, within pressure range B, the balloon element 16 in accordance with the present invention provides for compliant expansion within a range. The surgeon can select the optimal final adjusted balloon diameter by the proper selection of pressure. Following this adjustment, the balloon element 16 in accordance with the invention again becomes and remains at or near the adjusted diameter (Diam. "B") for subsequent inflations, if any, below the adjustment pressure, following the pressure/diameter curve labeled Diam. "B" in FIG. 5.

In accordance with the present invention, the inner layer 28, with which the outer layer 30 is joined, is made from a plastic polymeric material having high tensile strength and low initial distensibility. That inner layer 28, it has been found, can determine the expansion characteristic of the balloon element 16. The outer layer 30 is made from a plastic material which has desirable abrasion and puncture resistance and softness, and distensibility greater than that of the inner layer 28. For reasons explained below, having to do with the method of making the balloon element 16, it is also desirable that the material of the outer layer 30 have a melting point substantially lower than the melting point of the material of the inner layer 28.

Those skilled in the art and familiar with materials conventionally used in the manufacture of balloon elements for balloon catheters will appreciate that "high" in relation to the tensile strength of materials used for balloon elements such as the balloon elements 16 generally means burst strengths in excess of 40,000–65,000 pounds per square inch (psi).

In the presently preferred form of the invention, the inner layer 28 is made of polyetheretherketone (PEEK). It has been found that this material, which exhibits low initial distensibility and burst strength on the order of 30,000 to 100,000 psi and preferably 55,000 psi to 100,000, is uniquely and unexpectedly adaptable to use in balloon elements having the desired characteristics of the present invention. Specifically, when constructed in accordance with the present invention, balloon elements made of PEEK can provide an expansion characteristic approximating that the ideal illustrated in FIG. 5. It has been found that balloon elements 16 based upon an inner layer 28 of PEEK can be made to provide selective variations in diameter in small increments of from 0.05 to 0.5 millimeters in a non-compliant range, and large increments of 0.5 millimeters to 5 millimeters in the compliant range. In addition, by judicious design of the balloon element 16, transition pressures "P" can be placed within the range of 2 to 20 atmospheres, but more preferably, at from 8 to 12 atmospheres, a transition pressure which provides a finished balloon element of great versatility.

As will be more clear from the example set forth below, the inner layer 28 provides for the balloon element 16 the desired tensile strength and essentially determines the expansion characteristic of the balloon element. The outer layer 30, however, lends to the balloon element 16 a desired and highly desirably abrasion and puncture resistance. It also provides for the balloon element 16 a soft "feel", and provides a desired shape memory for the balloon element 16.

The outer layer 30, in accordance with the presently preferred form of the invention, is made from a polyether block copolymer (PEBAX), but may consist of a material selected from among: ABS (acrylonitrile butadiene styrene); ANS (acrylonitrile styrene); Delrin acetal; PVC (polyvinyl chloride); PEN (polyethylene napthalate); PBT (polybutylene terephthalate); polycarbonate; PEI (polyetherimide); PES (polyether sulfone); PET (polyethylene terephthalate); PETG (polyethylene terephthalate glycol), high and medium melt temperature: polyamides, aromatic polyamides, polyethers, polyesters, Hytrell, polymethylmethacrylate, polyurethanes: copolymers, EVA (ethylene vinyl acetate) or ethylene vinyl alcohol; low, linear low, medium and high density polyethylenes, latex rubbers, FEP, TFE, PFA, polypropylenes, polyolefins; polysiloxanes, liquid crystal polymers, inomers, Surlins, silicone rubbers, SAN (styrene acrylonitrile), nylons: 6, 6/6, 6/66, 6/9, 6/10, 6/12, 11, all PEBAXs 12; polyether block amides; thermoplastic elastomers and the like.

The walls of the balloon element 16 preferably have a combined thickness of between about 0.0002 and 0.001 inches, the most preferred thickness being about 0.0004 inches.

Various techniques for the making of balloon elements for catheters have been described in the prior art. For example, U.S. Pat. No. 5,264,260, issued Nov. 23, 1993, to Saab, describes a process for making a balloon element of PET using the steps of axially drawing and radially expanding a parison or piece of tubing to form a single-walled element. In U.S. Pat. No. 5,348,538, issued Sep. 20, 1994, to Wang et al., a process for making a balloon element consists of extruding a hollow tube, blow molding a balloon from the tube, and annealing the balloon, each of which steps is said to include a number of sub-steps. In U.S. Pat No. 5,270,086, issued Dec. 14, 1993, to Hamlin, it is suggested that a multi-layered balloon element be formed by co-extrusion of multiple polymers through a die.

The process by which balloon elements in accordance with the present invention are preferably made, and which constitutes an aspect of the present invention, will now be described in reference to a preferred embodiment of the balloon element 16 in which the inner layer 28 is of PEEK and the outer layer 30 is of PEBAX.

In this regard, PEEK tubing may be extruded using conventional equipment and techniques, and the PEEK tubing then provided with a top coating of the material desired for the outer layer 30. The material which ultimately forms the outer layer 30 may be applied to the PEEK tubing in a number of ways, but the presently preferred technique involves top coating of the material of the outer layer 30 over and onto the material of the inner layer in a secondary extrusion process, not unlike the way in which insulation is applied to electrical wire.

An example of the manufacture of a balloon element using the above-described process follows:

EXAMPLE

Extrusion

Tubing of polyetheretherketone (PEEK) was first extruded on a Killian extruder using conventional techniques and collected onto spools in adequate lengths to form multiple balloons (about 5000 feet). The PEEK tubing was fed into the back of an extruder die head, into the mandrel, and engaged into the melt line. A top coating of polyether block copolymer (PEBAX) was extruded concentrically with the tubing, the thickness of the top coating being determined and adjusted by the extruder screw speed and puller speed as well as the tooling geometry. The PEEK tubing, thus top-coated, was collected on a spool at the end of the extrusion line. Final dimensions of the resulting two layer tubing were 0.025 in×0.040 in.

Balloon Processing

Balloons were formed from the two layer tubing using conventional balloon blowing equipment including heated mold dies with a 3.5 mm×20 mm mold and a single forming operation. Pressures of 60 to 250 psi were used to form the balloons and heated for approximately 45 seconds. Thereafter the balloons were cooled (5 seconds) using convection cooling. Mold temperature was maintained at 270°±50° F. The tubing was axially oriented in its cooled state on the machine prior to blow molding in the secondary extrusion process; little or no additional axial orientation was needed during the secondary process.

Balloon Characteristics

The thus-formed 3.5 mm balloon, of dimension 0.033 in×0.041 in two layer balloon had a 0.0010 in to 0.0035 in double wall thickness. The PEEK inner layer provided approximately 25% of the thickness of the double wall, with the PEBAX providing approximately 75% of the remaining double thickness wall. Balloon feel and clarity were excellent and no delamination of one layer from the other was seen.

Puncture Resistance

The sharp point puncture forces on average were 1.0 lbs., as compared to an average 0.8 to 0.9 lbs. for an even thicker (0.004") balloon element made of polyethylene alone. In the dull or radiused point puncture test, the above-described PEEK/PEBAX balloon element was able to deliver 2.5 lbs., up form 2.3 lbs. uncoated. Where coated with polyurethane, PET delivered 2.25 lbs. Uncoated PET delivered 1.2 lbs. with identical overall wall thicknesses.

Figure 6:
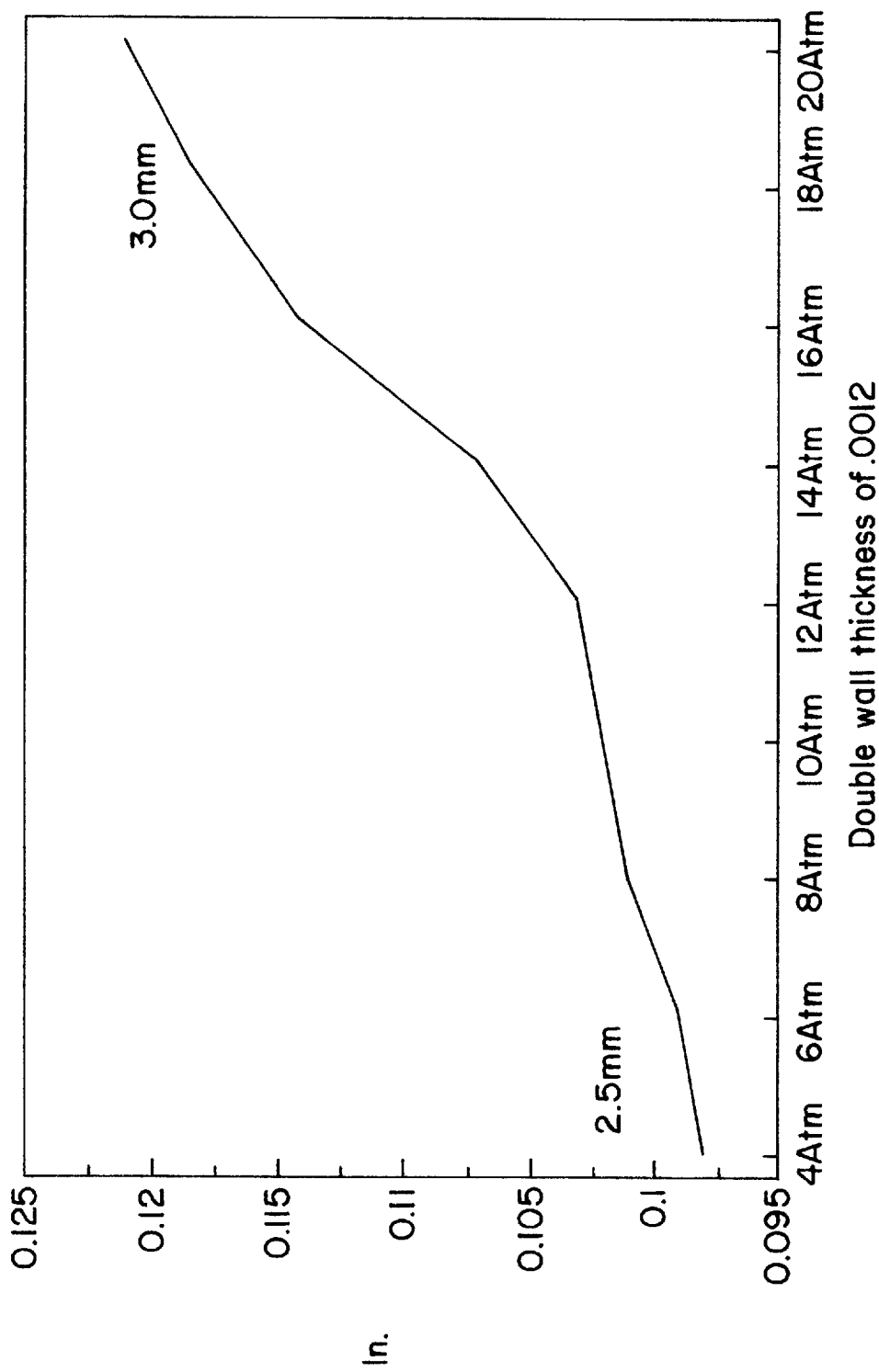
FIG. 6 is a graph depicting the expansion characteristics of an exemplary balloon in accordance with the invention.

FIG. 6 depicts the expansion characteristics of the exemplary balloon element described above.

In an alternative process for making a balloon element 16 the balloon element may be made by making and conjoining separate extrusions for the materials of the inner layer 28 and outer layer 30. For example, a balloon may first be created from an extrusion of PEEK taking, and a second, separate, tubular, extrusion may be made from polyethylene material. The polyethylene material may be crosslinked in a manner known to the art, by radiation for example, and expanded in a separate operation to create a heat shrinkable "shrink" tube. Placement of the shrink tube over the previously formed PEEK balloon, followed by heating of the shrink tube to cause it to shrink toward the diameter of the PEEK extrusion causes the polyethylene to provide an outer layer over the PEEK balloon. It will of course be realized that one could apply the above-described shrink tube technique to include additional layers over all or portions of the balloon to selectively modify balloon performance.

Figure 8:
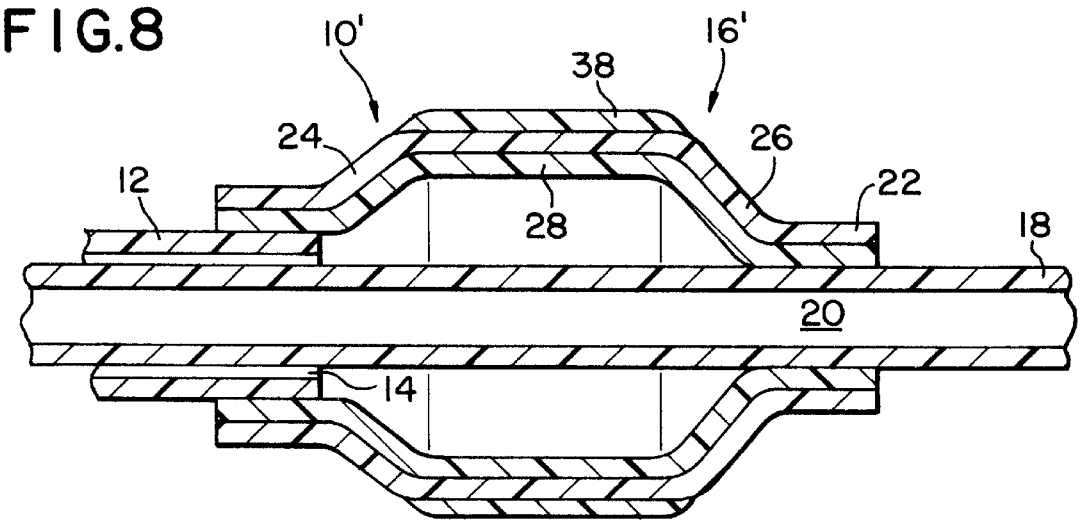
FIG. 8 is a side elevation view of a modified form of a balloon element in accordance with the invention.

Referring now to FIG. 8, for example, if it is desired to prevent rapid expansion of the central portion of the balloon element 16 during operation, one may provide an additional layer 32, of polyethylene, for example, in only the center portion 38 of the balloon. In such an arrangement, the presence of the additional polyethylene layer 32 serves to encourage the portions 34 and 36 of the balloon element 16 on either side of the center portion 38 to expand more rapidly than the center portion 38. Of course, it is not necessary that the additional layer 32 cover the entire surface of the inner layer 28, although in some, and perhaps most cases, this may be desirable. In any event, it should be realized that the above-described single-wall multiple-layer construction greatly increases the versatility and ultimate utility of the balloon element 16.

Figure 7:
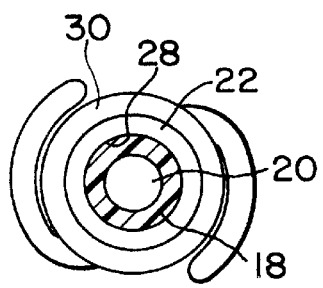
FIG. 7 is a transverse cross-sectional view, showing an expander balloon element in accordance with the present invention.

FIG. 7 illustrates a balloon catheter 10 with a two-layered balloon element 16 in the folded configuration it would have during delivery to the site of a lesion or during stent delivery. It has been found that the use of an outer layer 30, such as a layer of PEBAX, enhances the performance of the balloon element 16 in two ways: first, as is illustrated by the above example, by judicious selection of the material of the outer layer 30, the balloon element 16 may be made more resistant to puncture from external sources such as surgeon's instruments, calcified lesions, or even in some rare instances the stent. Second, the outer layer 30 tends to enhance the "shape memory" of the balloon element 16, so that when deflated the balloon element 16 tends to return to its original folded shape rather than form a single flat "wing". High pressure balloon elements heretofore known tend not to have enough shape memory to return to their original folded shapes after use.

It should be understood that the present invention may be embodied in other specific forms without departing from its spirit or essential attributes. Accordingly, reference should be made to the appended claims, rather than to the foregoing specification, for a determination of the scope of the invention.

What is claimed is:

1. A multilayered balloon for attachment to a medical catheter, comprising:

an inner layer;

an outer layer adhered to said inner balloon layer whereby said inner and said outer layer provide a laminated balloon wall;

said inner layer being made from plastic material having high tensile strength and low initial distensibility and said outer layer being made from a plastic material having abrasion resistance and distensibility greater than that of said inner layer;

said balloon characterized by a compliance characteristic described by a continuous nonlinear compliance curve, said compliance curve having a compliant initial inflation range, a transition point and a nonlinear, non-compliant second inflation range, whereby said initial inflation range is followed by said balloon during an initial phase of inflation of said balloon and said second inflation range is followed by said balloon during a second inflation phase of said balloon; and wherein said inner layer consists essential of polyetheretherketone.

2. An expander balloon in accordance with claim 1, wherein said outer layer is coextensive with the surface of said inner layer.

3. An expander balloon in accordance with claim 2, wherein said outer layer consists essentially of a material selected from the group consisting of: ABS (acrylonitrile butadiene styrene); ANS (acrylonitrile styrene); Delrin acetal; PVC (polyvinyl chloride); PEN (polyethylene napthalate); PBT (polybutylene terephthalate); polycarbonate; PEI (polyetherimide); PES (polyether sulfone); PET (polyethylene terephthalate); PETG (polyethylene terephthalate glycol), high and medium melt temperature: polyamides, aromatic polyamides, polyethers, polyesters, Hytrell, polymethylmethacrylate, polyurethanes: copolymers, EVA (ethylene vinyl acetate) or ethylene vinyl alcohol; low, linear low, medium and high density polyethylenes, latex rubbers, FEP, TFE, PFA, polypropylenes, polyolefins; polysiloxanes, liquid crystal polymers, inomers, Surlins, silicone rubbers, SAN (styrene acrylonitrile), nylons: 6, 6/6, 6/66, 6/9, 6/10, 6/12, 11, all PEBAXs 12; polyether block amides; and thermoplastic elastomers.

4. An expander balloon in accordance with claim 1, wherein said inner layer consists essentially of polyetheretherketone and said outer layer consists essentially of PEBAX.

5. An expander balloon in accordance with claim 1, wherein said transition point on the compliance curve between said compliant initial inflation range and said non-compliant second inflation range is at about 2 to about 20 atmospheres.

6. An expander balloon in accordance with claim 5, wherein said transition point is at about 8 to about 12 atmospheres.

7. An expander balloon in accordance with claim 5, wherein said inner balloon layer consists essentially of polyetheretherketone and said outer balloon layer consists essentially of a plastic polymeric material having a melting point lower than polyetheretherketone.

8. An expander balloon in accordance with claim 1, wherein said inner layer consists essentially of an extruded tubular film having an uninflated cross-section comprising a plurality of circumferentially spaced lobes;

said outer layer comprising a secondary extrusion overlying said inner layer and maintaining the cross-section of said outer layer when the balloon is in an uninflated state, whereby folding of the balloon is facilitated.

9. A method of using an expander balloon attached to a medical catheter to place and implant a stent in a bodily vessel, the balloon having a low pressure diameter and a compliance characteristic described by a continuous nonlinear compliance curve having a compliant initial range and a non-compliant second range, the stent surrounding the expander balloon, comprising the steps of:

pressurizing the balloon to a first inflation pressure to inflate the balloon beyond its low pressure diameter, the balloon increasing in diameter to a first predetermined diameter in the initial range along the compliance curve corresponding to the first inflation pressure, and in so doing expanding the stent to a first stent diameter in which the stent is placed in the bodily vessel; and increasing the pressure applied to the balloon to a second inflation pressure sufficient to cause the balloon to increase further in diameter to a second predetermined diameter in the second range along the compliance curve corresponding to the second inflation pressure, whereby the diameter of the stent is expanded post-placement to implant the stent in the bodily vessel; and wherein said balloon is a multilayered balloon for attachment to a medical catheter, comprising:

an inner layer;

an outer layer adhered to said inner balloon layer whereby said inner and said outer layer provide a laminated balloon wall;

said inner layer being made from plastic material having high tensile strength and low initial distensibility and said outer layer being made from a plastic material having abrasion resistance and distensibility greater than that of said inner layer;

said balloon characterized by a compliance characteristic described by a continuous nonlinear compliance curve, said compliance curve having a compliant initial inflation range, a transition point and a nonlinear non-compliant second inflation range, whereby said initial inflation range is followed by said balloon during an initial phase of inflation of said balloon and said second inflation range is followed by said balloon during a second inflation phase of said balloon.

* * * * *